US010806345B2

(12) United States Patent
Kruiskamp

(10) Patent No.: US 10,806,345 B2
(45) Date of Patent: Oct. 20, 2020

(54) APPARATUS AND METHOD FOR MONITORING A PHYSIOLOGICAL PARAMETER

(71) Applicant: Dialog Semiconductor B.V., s-Hertogenbosch (NL)

(72) Inventor: Marinus Wilhelmus Kruiskamp, 's-Hertogenbosch (NL)

(73) Assignee: Dialog Semiconductor B.V., 's-Hertogenbosch (NL)

( * ) Notice: Subject to any disclaimer, the term of this patent is extended or adjusted under 35 U.S.C. 154(b) by 627 days.

(21) Appl. No.: 15/620,933

(22) Filed: Jun. 13, 2017

(65) Prior Publication Data

US 2018/0353074 A1    Dec. 13, 2018

(51) Int. Cl.
*A61B 5/00*     (2006.01)
*A61B 5/024*    (2006.01)

(52) U.S. Cl.
CPC ........ *A61B 5/0059* (2013.01); *A61B 5/02416* (2013.01); *A61B 5/02427* (2013.01)

(58) Field of Classification Search
None
See application file for complete search history.

(56) References Cited

U.S. PATENT DOCUMENTS

| | | | | |
|---|---|---|---|---|
| 4,258,719 A | * | 3/1981 | Lewyn | A61B 5/02416 307/650 |
| 4,928,248 A | * | 5/1990 | Takahashi | H01S 5/042 372/33 |
| 2011/0137181 A1 | * | 6/2011 | Lin | A61B 5/02427 600/479 |
| 2015/0102209 A1 | * | 4/2015 | Xu | G01J 1/44 250/214 LS |
| 2016/0025777 A1 | * | 1/2016 | Deliwala | G01J 1/44 324/115 |
| 2016/0038096 A1 | * | 2/2016 | Kim | A61B 5/7278 600/479 |
| 2016/0143566 A1 | * | 5/2016 | Ballam | A61B 5/14552 600/324 |
| 2016/0351119 A1 | * | 12/2016 | Ono | H01L 51/56 |

OTHER PUBLICATIONS

"Integrated Optical Module with Ambient Light Rejection and Three LEDs," Analog Devices Data Sheet, ADPD174GGI, Copyright 2015 Analog Devices, Inc., 3 pgs.
"AFE4403 Ultra-Small, Integrated Analog Front-End for Heart Rate Monitors and Low-Cost Pulse Oximeters," Texas Instruments, SBAS6S0B, May 2014, 99 pgs.

* cited by examiner

*Primary Examiner* — Pascal M Bui Pho
*Assistant Examiner* — Farouk A Bruce
(74) *Attorney, Agent, or Firm* — Saile Ackerman LLC; Stephen B. Ackerman

(57) ABSTRACT

An apparatus for monitoring a physiological parameter over a plurality of measurement periods is presented. The apparatus includes a circuit coupled to a light emitter and to a light receiver. The circuit is adapted to drive the light emitter with a constant first charge over the plurality of measurement periods. Also presented is a wearable device provided with an apparatus for monitoring a physiological parameter over a plurality of measurement periods. Also presented is a method for monitoring a physiological parameter over a plurality of measurement periods, the steps include providing a light emitter and a light receiver and driving the light emitter with a constant first charge over the plurality of measurement periods.

25 Claims, 7 Drawing Sheets

APPARATUS AND METHOD FOR MONITORING A PHYSIOLOGICAL PARAMETER

TECHNICAL FIELD

The invention relates to an apparatus and methods for monitoring a physiological parameter. In particular, the invention relates to a low power optical apparatus suitable for use with a wearable device.

BACKGROUND

An increasing number of wearable devices such as fitness bands are provided with a heart rate monitor. The heart rate can be measured by photoplethysmography, PPG, in which the skin of a subject is illuminated, usually using red or infrared light, and the transmitted or reflected light is captured to measure a change in light absorption. Since the amount of light absorbed will depend predominantly on the amount of blood present in the skin, changes in blood flow can be detected. In particular, light entering the body will scatter in a predictable manner as the blood flow dynamics changes. Various parameters can be derived from a PPG signal, including the heart rate of a subject, the maximum volume of oxygen VO2 max the subject can use, blood oxygen levels, blood pressure, and cardiac efficiency.

Current optical heart-rate monitors have a relatively high power consumption, limiting their usability. For example, continuous 24 hours/day monitoring requires frequent battery re-charge or the use of relatively large batteries unsuitable with wearable devices. Furthermore, present systems require LEDs having a forward voltage of approximately 3V, which might exceed the battery voltage when the battery ages. This affects the accuracy of the LED current and degrades the performance of the system significantly.

SUMMARY

It is an object of the invention to address one or more of the above-mentioned problems. According to a first aspect of the disclosure, there is provided an apparatus for monitoring a physiological parameter over a plurality of measurement periods, the apparatus comprising a circuit coupled to a light emitter and to a light receiver; the circuit being adapted to drive the light emitter with a constant first charge over the plurality of measurement periods. For example, the circuit may be a signal conditioning circuit such as an analog front end.

Optionally, the circuit may be adapted to provide the first charge to the light emitter over a measurement period and to integrate a second charge generated by the light receiver over the measurement period; wherein the first charge provided over the measurement period is substantially equal to another first charge provided to the light emitter over another measurement period.

Optionally, the circuit comprises a first energy storage element coupled to a voltage reference via a first switch to drive the light emitter.

Optionally, the circuit comprises an integrator coupled to the light receiver to integrate an AC component of the second charge.

Optionally, the circuit comprises a second energy storage element coupled to the voltage reference via a second switch to subtract a DC component of the second charge.

Optionally, the first constant charge may be proportional to a voltage provided by the voltage reference. For example, the first charge may comprise a product of a reference voltage with a capacitance of the first energy storage element and the second energy storage element.

Optionally, the second energy storage element may be adjustable.

Optionally, the integrator may be coupled to the light receiver; the light receiver comprising a first terminal and a second terminal; and wherein the light emitter is coupled to the first terminal via the first energy storage element, and to the second terminal via the second energy storage element.

Optionally, the integrator comprises an operational amplifier coupled to a capacitor.

Optionally, the apparatus comprises a calibration circuit for cancelling a background current generated by the light receiver.

Optionally, the calibration circuit comprises a sample and hold circuit coupled to a current source.

According to a second aspect of the disclosure, there is provided a wearable device comprising an apparatus for monitoring a physiological parameter over a plurality of measurement periods, the apparatus comprising a circuit coupled to a light emitter and to a light receiver; wherein the circuit is adapted to drive the light emitter with a constant first charge over the plurality of measurement periods.

The wearable device according to the second aspect of the disclosure may comprise any of the features described above in relation to the apparatus according to the first aspect of the disclosure.

According to a third aspect of the disclosure, there is provided a circuit for use with a light emitter and a light receiver, the circuit being adapted to drive the light emitter with a constant first charge over a plurality of measurement periods. For example, the circuit may be a signal conditioning circuit such as an analog front end.

Optionally, the circuit comprises a first energy storage element coupled to a voltage reference via a first switch to drive the light emitter.

Optionally, the circuit comprises an integrator coupled to the light receiver.

Optionally, the circuit comprises a second energy storage element coupled to the voltage reference via a second switch.

According to a fourth aspect of the disclosure, there is provided a method for monitoring a physiological parameter over a plurality of measurement periods, the method comprising providing a light emitter and a light receiver; and driving the light emitter with a constant first charge over the plurality of measurement periods.

Optionally, the method comprises providing the first charge to the light emitter over a measurement period and integrating a second charge generated by the light receiver over the measurement period; wherein the first charge provided over the measurement period is substantially equal to another first charge provided to the light emitter over another measurement period.

Optionally, the second charge comprises an AC component and a DC component; the method comprising integrating the AC component to obtain an integrated signal. For example, the integrated signal may be a voltage.

Optionally, the method comprises deriving the physiological parameter based on the integrated signal.

Optionally, the method comprises subtracting the DC component, wherein subtracting the DC component is performed passively.

Optionally, subtracting the DC component comprises charging a second energy storage element coupled to the light emitter.

Optionally, providing the first charge comprises charging a first energy storage element coupled to the light emitter to increase a voltage across the light emitter.

Optionally, the method comprises a reset phase for charging the first energy storage element and the second energy storage element.

Optionally, the method comprises cancelling a background current generated by the light receiver.

Optionally, the constant first charge may be proportional to a reference voltage.

BRIEF DESCRIPTION OF THE DRAWINGS

The invention is described in further detail below by way of example and with reference to the accompanying drawings, in which.

DETAILED DESCRIPTION

Figure 1:
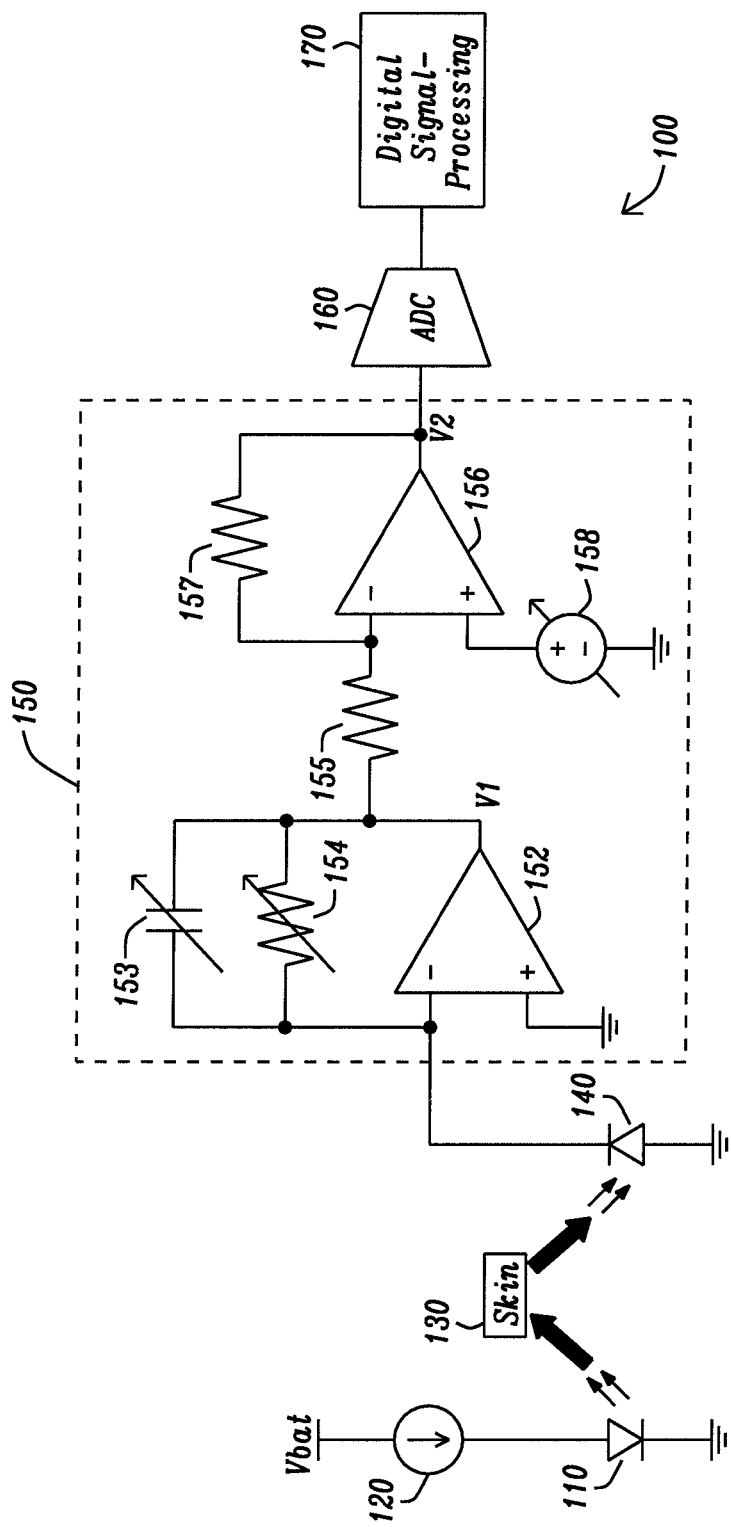
FIG. 1 is a schematic diagram of a conventional optical heart-rate monitoring system.

FIG. 1 illustrates an optical heart-rate monitoring system 100 according to the prior art.

The system 100 includes a light emitting diode LED 110 for emitting light towards a skin area of a subject 130, and a photodiode 140 for receiving scattered light from the skin sample 130. The LED 110 is connected to a current source 120 for delivering a constant current. An analog front end AFE 150 has an input connected to the photodiode 140 and an output connected to an analog to digital converter ADC 160. The ADC 160 is connected to a digital signal processing 170.

The AFE 150 includes a trans-impedance-amplifier TIA connected to a gain-amplifier. The TIA is formed by operational amplifier 152, variable resistance 154 and variable capacitor 153. The gain-amplifier is formed by operational amplifier 156 and resistances 155 and 157. The operational amplifier 152 has an inverting input connected to the photodiode 140 and a non-inverting input connected to the ground. An output of the operational amplifier 152 is connected to the non-inverting input via the variable resistance 154 and a variable capacitor 153 arranged in parallel. The operational amplifier 156 has an inverting input connected to the output of the TIA via the resistor 155 and a non-inverting input connected to a variable voltage source 158. The output of the operational amplifier 156 is connected to the non-inverting input via the resistance 157. The output of the operational amplifier 156 is connected to the ADC 160. An output of the ADC is connected to the digital signal processing 170.

In operation, the light emitted by the LED 110 is driven by a constant current from the current source 120. The light emitted by the LED 110 is reflected by the skin 130 onto the photodiode 140. The reflected light is measured with a high repetition rate, typically a 100 times a second, in order to accurately derive the heart-rate of the subject.

At the start of each measurement, the LED 110 is turned on. The light reflected by the skin sample 130 is absorbed by the photodiode 140. This causes a current I to flow through the photodiode 140. This current is then converted into a voltage V1 by the TIA. The voltage V1 has a large DC-component. The gain-amplifier together with the variable voltage source 158, are used to subtract the DC component and amplify the remaining AC component of the voltage V1. The AC voltage V2 is then converted into a digital signal by the ADC 160. This digital signal is then further processed by the digital signal processing 170.

In order to obtain accurate measurements, the output voltage V2 of the AFE 150 must be completely settled and stable. This requires the current through the LED 110 to be accurate and stable. It also requires that the ADC has enough time to sample the voltage V2. To achieve this, all components of the systems, including the LED 110 must be active for at least several microseconds. The light emitted by the LED 110 should also be significantly stronger than the ambient light. To obtain a sufficient intensity of emitted light, the LED 110 is therefore driven with a large current, in the order of 40 mA by the current generator 120. The energy associated with the LED 110 can be more than 1 uJ per measurement (10 µs×40 mA×3V=1.2 µJ). Considering that the system performs 100 measurements per second this results in an average power consumption of 0.1 mW. In addition, one must take into account the power-consumption of the low-noise TIA 152, the variable voltage generator 158 (DC-removal), the gain-amplifier 156, the ADC 160 and the signal processing 170.

Figure 2:
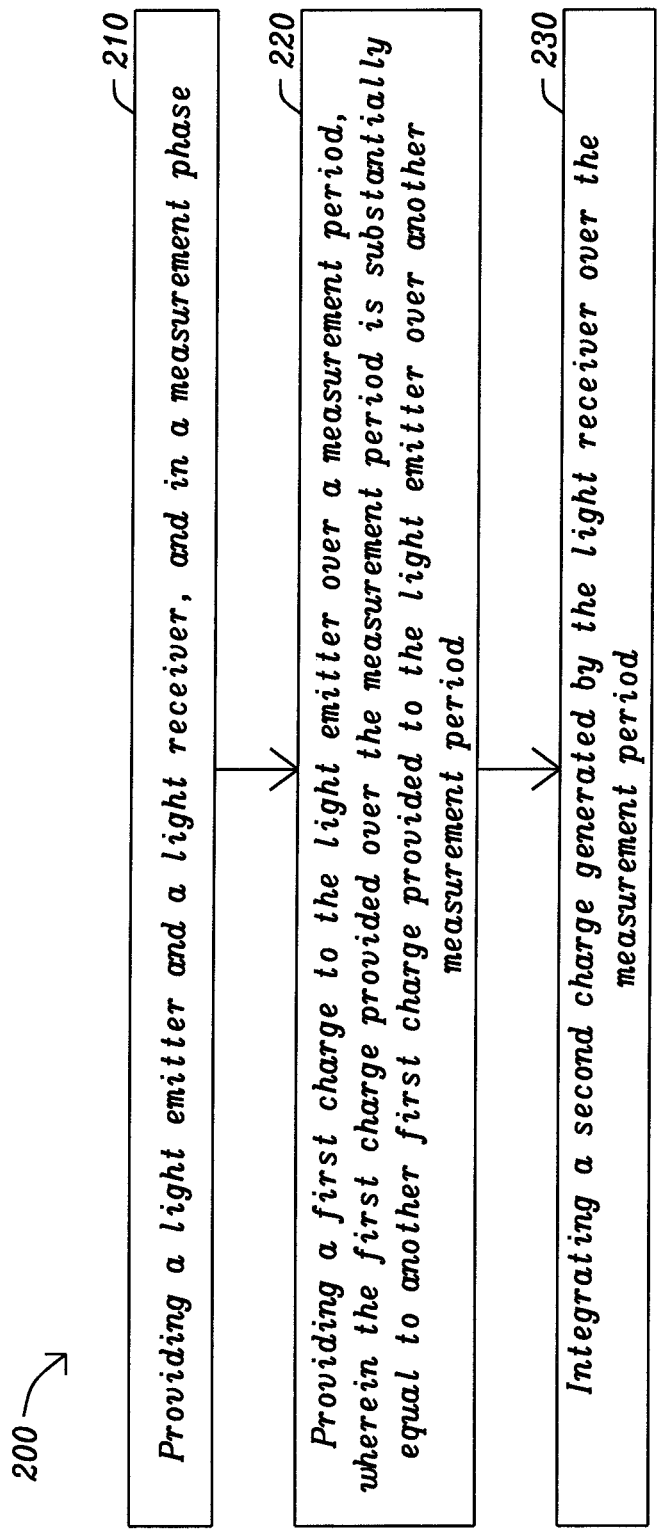
FIG. 2 is a flow chart of a method for monitoring a physiological parameter of a subject.

FIG. 2 illustrates a method 200 for monitoring a physiological parameter of a subject. The method is based on providing a light emitter and a light receiver; and driving the light emitter with a constant first charge over the plurality of measurement periods.

At step 210, a light emitter and a light receiver are provided. At step 220, a first charge is provided to the light emitter over a measurement period. The first charge provided over the measurement period is substantially equal to another first charge provided to the light emitter over another measurement period.

At step 230, a second charge generated by the light receiver over the measurement period is integrated. The second charge may comprise an AC component and a DC component. For example, the DC component can be subtracted and the remaining AC component integrated to obtain an integrated signal, such as a voltage signal. In a subsequent step, a physiological parameter can be derived based on the integrated signal.

Using the method 200, it is possible to monitor a physiological parameter of a subject over an extended period of time, while consuming relatively little energy. For instance, the physiological parameter may be a heart rate of a subject. The method may be implemented on a wearable device like a fitness band provided with a small battery.

Figure 3:
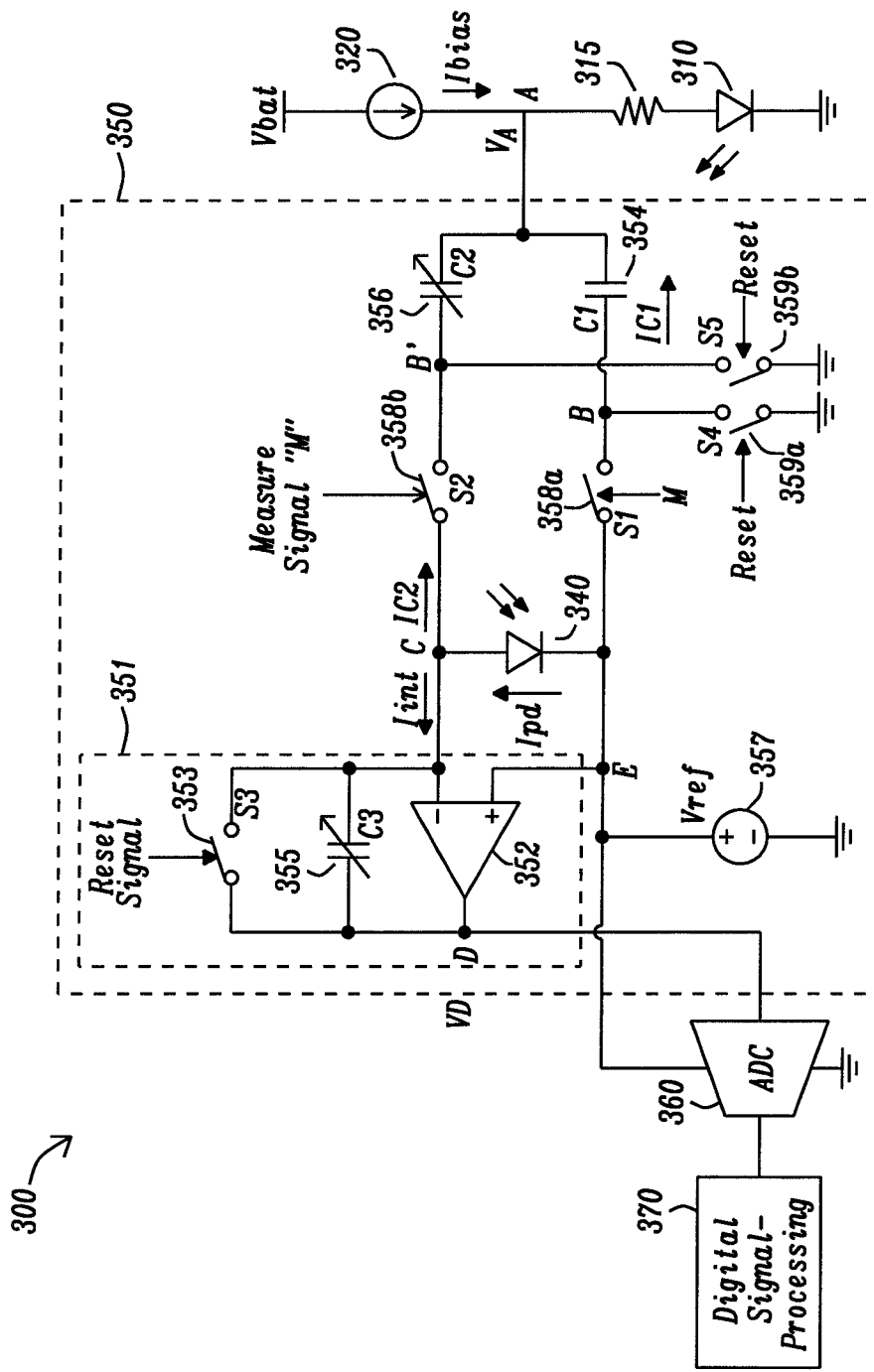
FIG. 3 is an apparatus for monitoring a physiological parameter according to the method of FIG. 2.

FIG. 3 illustrates an apparatus 300 for monitoring a physiological parameter according to the method 200 of FIG. 2. The apparatus comprises a signal conditioning circuit 350, coupled to a light emitter 310, and to a light receiver 340. In this example, the light emitter 310 is provided by a light emitting diode LED for emitting light towards a skin area, not shown. The light receiver 340 is provided by a photodiode for receiving scattered light from the skin area. The light emitter and the light receiver may be arranged either in a reflection geometry or in a transmission geometry. The signal conditioning circuit 350 is coupled to a digital signal processing unit 370 via an ADC 360.

The LED 310 is connected in series with a current source 320 via an optional resistance 315. The current source 320 is connected to a battery voltage Vbat. The resistance 315 has a first end coupled to the current source 320 via a node A, and a second end coupled to a first terminal (anode) of the LED 310. The LED 310 has a second terminal (cathode) coupled to a ground.

The signal conditioning circuit 350 comprises a charge-integrator 351 also referred to as charge-to-voltage converter, a first energy storage element 354, and a second energy storage element 356. The charge-integrator 351 is coupled to a voltage source also referred to as voltage reference 357 to provide a reference voltage Vref. The first energy storage element 354 is coupled to the voltage reference 357 via a first switch S1 358a, and the second energy storage element 356 is coupled to the voltage reference 357 via a second switch S2, 358b. In this example, the first energy storage element is provided by capacitor C1, and the second energy storage element is provided by variable capacitor C2. The switches S1 and S2 are also referred to as measurement switches.

The signal conditioning circuit 350 has an input coupled to the node A and an output coupled to an analog to the digital converter ADC 360. The ADC 360 has a first input for receiving the output of the signal conditioning circuit, a second input for receiving the reference voltage Vref and an output coupled to a digital signal processing unit 370.

For example, the charge-integrator 351 may be provided by an operational amplifier 352 having a first input, for example a non-inverting input and a second input for example an inverting input, and an output at node D. The first input is coupled to the output via a capacitor C3 355, hence forming a feedback loop. A third switch S3 353 is coupled in parallel with the capacitor C3 355. The capacitor C3 may be a variable capacitor allowing to adjust the gain of the charge-integrator 351.

The first input of the operational amplifier 352 is coupled to the first capacitor 354 via the first switch S1, 358a; and the second input is coupled to the second capacitor 356 via the second switch S2, 358b.

The first capacitor C1, 354 and the first switch S1, 358a are coupled to a fourth switch S4 359a via a node B. The third switch S4 359a has a first terminal coupled to the node B and a second terminal coupled to a ground. The second capacitor C2, 356 and the second switch S2, 358b are coupled to a fifth switch S5 359b via a node B'. The fifth switch S5 359b has a first terminal coupled to the node B' and a second terminal coupled to a ground. The switches S3, S4 and S5 are also referred to as reset switches. The first capacitor C1 354 has a first terminal coupled to node A and a second terminal coupled to node B. The second capacitor C2 356 has a first terminal coupled to node A and a second terminal coupled to node B'.

The photodiode 340 has a first terminal, for example an anode, and a second terminal, for example a cathode. The first terminal is coupled to the second input of the operation amplifier 352 and to the second switch S2 358b at node C. The second terminal is coupled to the first input of the operation amplifier 352 and to the first switch S1 358a at node E. The voltage reference 357 has a first terminal couple to the node E and a second terminal coupled to the ground. The output of the charge-integrator 351 is coupled to an input of the ADC 360. An output of the ADC 360 is coupled to the digital signal processing unit 370.

In another embodiment, the circuit 300 is provided with a plurality of light emitters arranged in parallel between the node A and the ground. In this case series resistors are provided to balance the current flowing through each individual light emitter.

Figure 4:
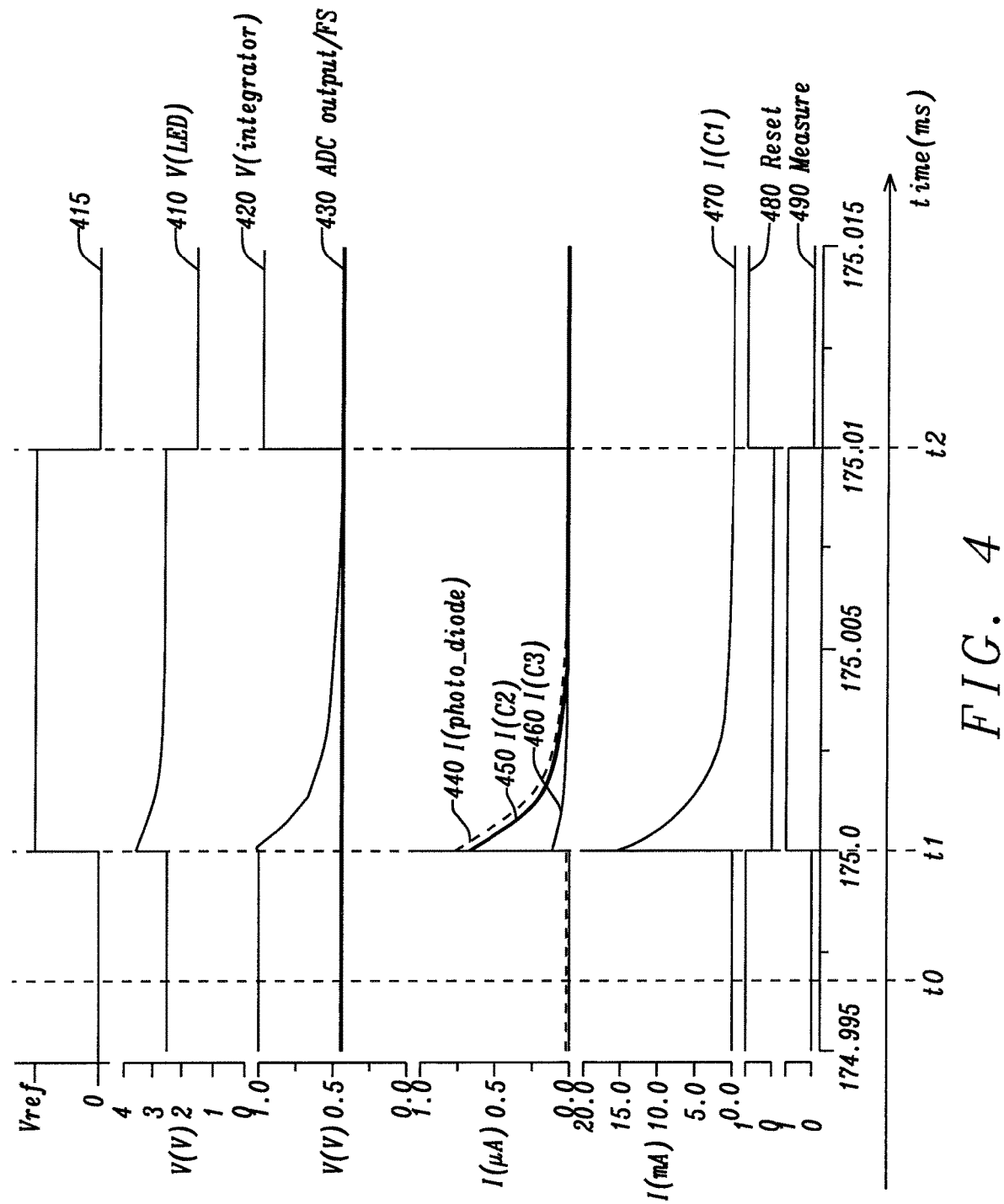
FIG. 4 is a time chart illustrating the working of the apparatus of FIG. 3 over a time window spanning 20 µs.
Figure 5:
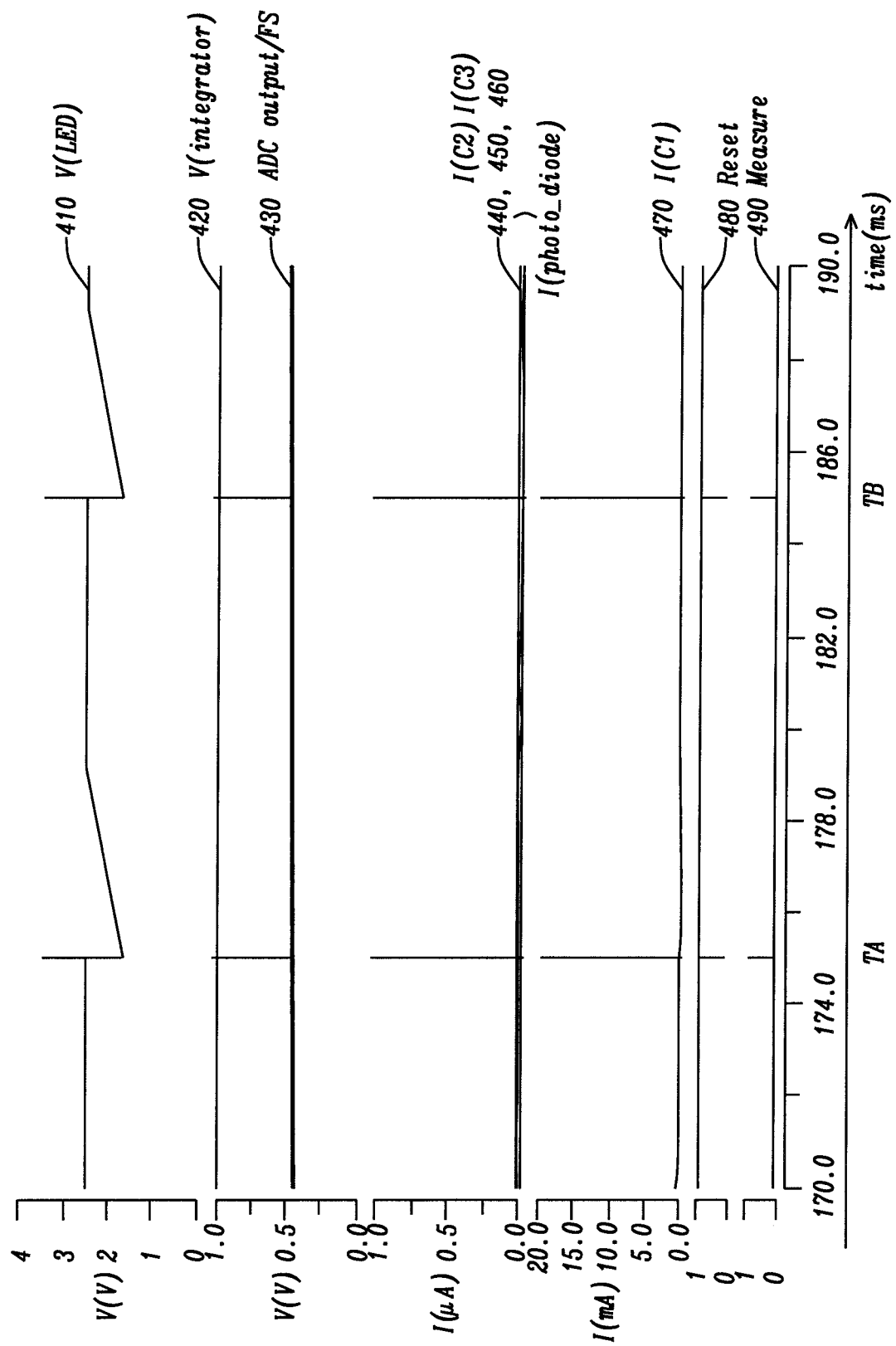
FIG. 5 is a time chart illustrating the working of the apparatus of FIG. 3 over a time window spanning 20 ms.
Figure 6:
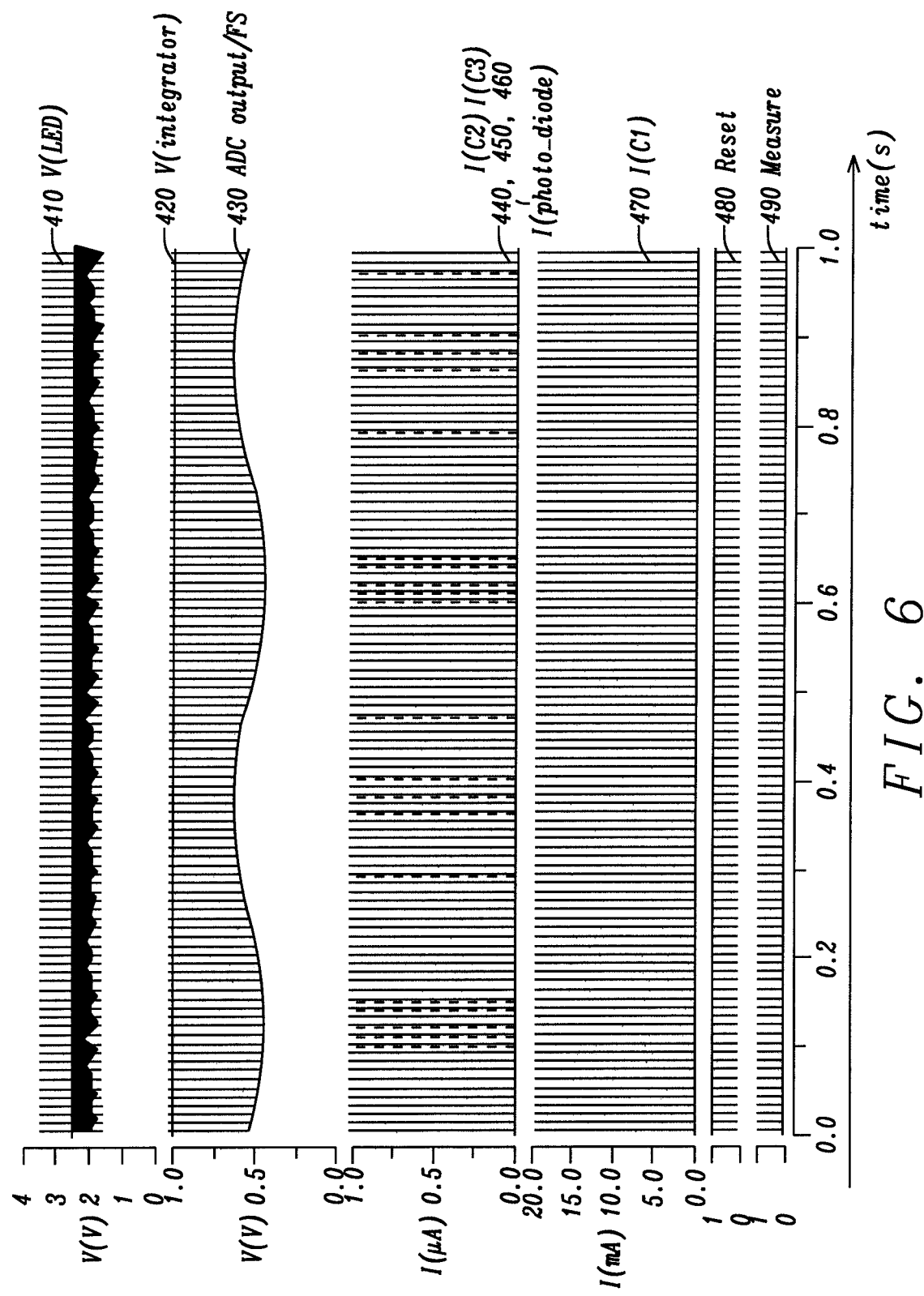
FIG. 6 is a time chart illustrating the working of the apparatus of FIG. 3 over a time window spanning 1 s.

FIGS. 4, 5 and 6 illustrate the working of the apparatus of FIG. 3 by providing simulation results for three different time windows. The apparatus of FIG. 3 operates over a plurality of cycles, each cycle being defined by a reset phase and a measurement phase. In these simulations, the photo-diode is modelled by a diode in parallel with a current-controlled current source, with an average coupling between LED and the photo-diode equal to 1/20000 and then modulated by 2% with a frequency of 2 Hz, reflecting a high heart-rate of 120 beats/minute. The reference voltage is set to 1V and the capacitor C1 to 22 nF. The maximum current is limited with a 50 Ohm resistor resulting in a maximum current of 20 mA. The total charge into the LED per cycle is equal to 1V×22 nF=22 nC (this is the same charge as a 20 mA pulse during 1.1 us). The capacitors C2 and C3 have a capacitance of 1 pF and 0.2 pF respectively.

FIG. 4 is a time chart showing a plurality of signals over a time window spanning 20 μs and including a measurement phase of a cycle. The signals include: the voltage VA 410 at node A, the voltage VB 415 at node B, the voltage VD 420 at the output of the charge-integrator, the output voltage 430 of the ADC, the current 440 across the photodiode; the current 450 across the capacitor C2; the current 460 across the capacitor C3; the current 470 across the capacitor C1, the reset logic signal 480, and the measure logic signal 490.

Before time t1, for instance at time t0, the system is in the reset phase. The reset signal 480 is high for example logic 1, hence closing the switches S3, S4 and S5. The measure signal 490 is low and the switches S1 and S2 are open. In the reset phase, the current generator 320 provides a small bias current to the LED 310. As a result, the LED 310 only emits a very weak light beam. The voltage 410 at node A is stable. For example, VA has a constant value of circa 2.5V. The output voltage VD 420 of the charge-integrator is also stable. For example, VD has a constant value of circa 1V. The currents 470, 450, 460 through the capacitors C1, C2, C3 are null. The photodiode may generate a current due to the presence of ambient light. Such a current can be subtracted.

At time t1, the system enters the measurement phase. During the measurement phase, a voltage step equal to Vref is applied on node A via the capacitor C1. The reset signal 480 is low for example logic 0, hence opening the switches S3, S4 and S5. The measure signal 490 is high and the switches S1 and S2 are closed. The voltage source 357 charges the capacitors C1 and C2 hence increasing the voltage at nodes B and B' as shown by signal 415. Such an increase in voltage is also referred to as a voltage step. The voltage VB' at node B' is almost identical to the voltage VB at node B due to the high gain of operational amplifier 352. The voltages VB and VB' remain constant between times t1 and t2 and equal to Vref. The voltage VA 410 also increases hence causing an increase in the current 440 in the LED 310. For example, VA increases to about 3.5 V.

The current in the LED 310 is equal to the sum of the current 450 through the capacitor C2 and the current 470 through the capacitor C1. The current through the LED 310 is a current pulse which decays between times t1 and t2. Therefore, during the measurement phase, the current through the LED is not constant. However, the charge $Q_{LED}$, also referred to as charge pulse received by the LED during a measurement period, for instance between times t1 and t2, remains substantially constant from one measurement period to the next. For example, if the system carries out N measurements through N measurement phases, the charge received by the LED during the first measurement phase will be approximately the same as the charge received by the LED during the $N^{th}$ measurement. The current 440 through the photodiode 340 also increases at time t1 and decreases between times t1 and t2.

At time t1, the voltage VD 420 starts decreasing. Between times t1 and t2 the output voltage VD decreases until the voltage VA has returned to its initial reset value. Such a voltage drop may be explained as follows. The charge $Q_{LED}$ flowing through the LED 310 can be expressed as:

$$Q_{LED} = V_{REF}(Cap_1 + Cap_2) \quad (1)$$

In which $Cap_1$ and $Cap_2$, are the capacitances of capacitors C1 and C2 respectively. Typically, $Cap_1$ is much greater than $Cap_2$. For example, $Cap_1$ may range between about 10 nF and about 100 nF, and $Cap_2$ may range between about 100 fF to about 100 pF. The charge $Q_{LED}$ is therefore proportional to Vref. Since the charge $Q_{LED}$ depends only of constant values Vref, $Cap_1$, $Cap_2$, the charge $Q_{LED}$ is also substantially constant.

Inside the LED, each electron of $Q_{LED}$ will generate a photon. Some of these photons are reflected by the skin and come into the active area of the photo-diode 340. Each photon absorbed by the photo-diode 340 will generate exactly one electron contributing to the current 440 through the photodiode. The charge $Q_{Photodiode}$ flowing through the photodiode 340 can be expressed as the sum of a charge $Q_{Skin}$ generated by the photon reflected from the skin, and a charge $Q_{Ambient}$ generated by ambient light as:

$$Q_{Photodiode} = Q_{Skin} + Q_{Ambient} \quad (2)$$

Figure 7:
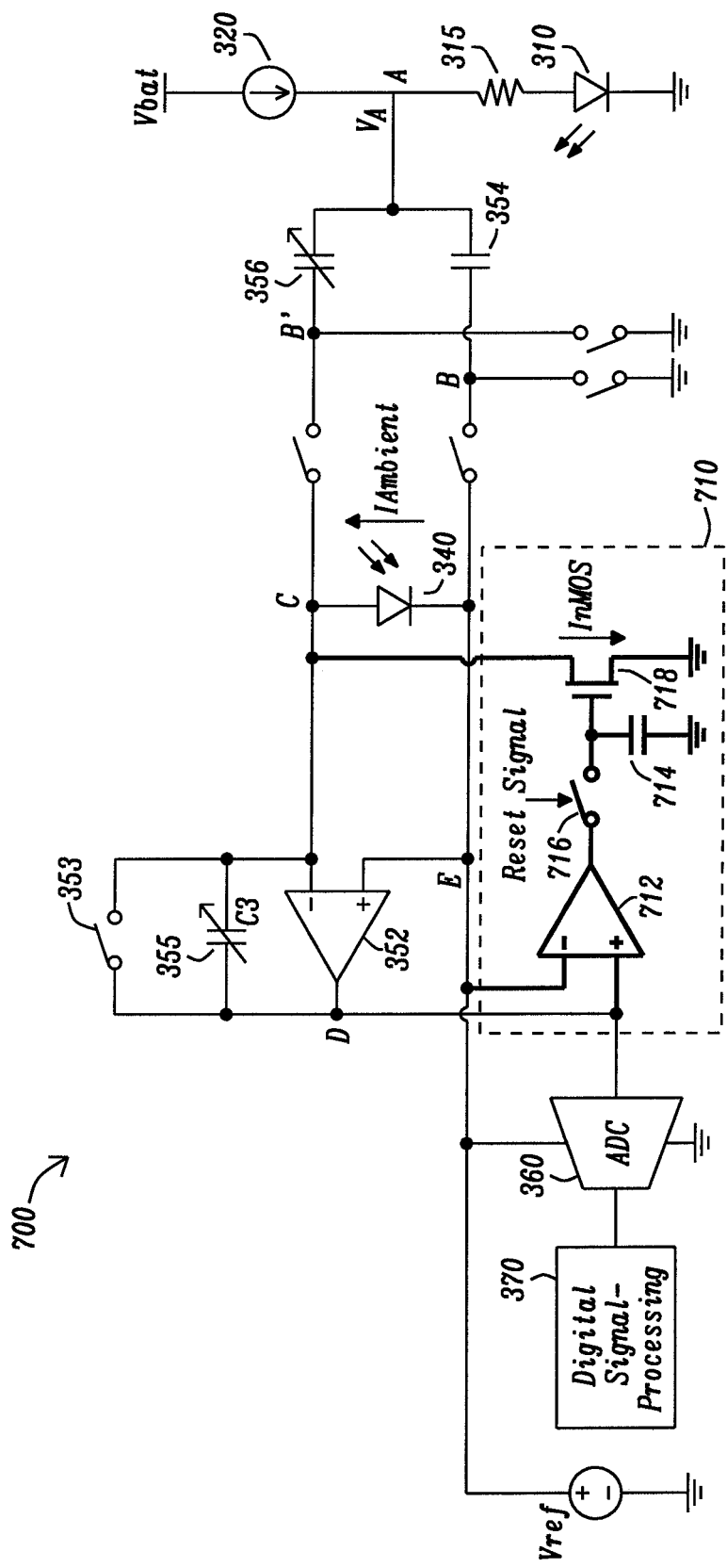
FIG. 7 is another apparatus for monitoring a physiological parameter of a subject.

The charge $Q_{Ambient}$ can be subtracted, such that the only charge coming out of the photodiode 340 is $Q_{Skin}$. The charge associated with ambient light may be cancelled in different ways. For example, two measurements may be performed, a first (background) measurement without activation of the LED, and a second measurement with activation of the LED. The background measurement can then be subtracted from the second measurement. Another approach is to provide an additional circuit for subtracting $Q_{Ambient}$, as shown in FIG. 7 below.

When a photon reflected by the skin is absorbed by the photodiode 340, the charge $Q_{Skin}$ flows from the photodiode 340 into node C. Such a charge can be expressed as a function of a reflection coefficient R of the skin as:

$$Q_{Skin} = RQ_{LED} = Q_{AC} + Q_{DC} \quad (3)$$

The reflection coefficient R has a large DC component, $R_{DC}$ and a small AC component $R_{AC}$ which is due in part to variations in blood flow associated with heart beats. The charge $Q_{Skin}$ is therefore the sum of a AC component $Q_{AC}$ and a DC component $Q_{DC}$. To prevent overloading the integrator 351, the $Q_{DC}$ component may be subtracted. This allows using a small integration capacitor C3, therefore providing sufficient gain in the integrator 351 to obtain a relatively large output voltage VD.

The subtraction of the component $Q_{DC}$ may be achieved using the charge $Q_{Replica}$ flowing through the capacitor C2, and defined as $Q_{Replica} = V_{REF} Cap_2$. The charge $Q_{Int}$, flowing through the integrator is then defined as:

$$Q_{Int} = Q_{Photodiode} - Q_{Replica} \quad (4)$$

$$Q_{Int} = V_{REF}(R(Cap_1 + Cap_2) - Cap_2) \quad (5)$$

The capacitance $Cap_2$ of the capacitor C2 may be adjusted such that $Q_{Replica} = Q_{DC}$. In this way the DC component $Q_{DC}$ is subtracted.

The charge $Q_{Int}$, flowing through the integrator causes a voltage drop at node D. The voltage drop at node D can be expressed as:

$$\Delta V(D) = \frac{-Q_{Int}}{Cap_3} = \frac{-V_{REF}(R(Cap_1 + Cap_2) - Cap_2)}{Cap_3} \quad (6)$$

By converting the voltage drop with the ADC and using $V_{REF}$ as a reference for the ADC, then a digital signal also referred to as digital code, DCode, can be obtained as:

$$DCode = \frac{-(R(Cap_1 + Cap_2) - Cap_2)}{Cap_3} \quad (7)$$

Using this approach, it is possible to obtain a measurement of the modulation of the reflection coefficient R.

Referring to equation (7), one can observe that the digital signal depends only on the reflection coefficient R, and on the capacitances Cap1, Cap2 and Cap3. The digital signal is therefore independent of time, voltage, current, resistance or temperature. As a result, this approach does not require an accurate time reference or precise voltages and currents. For example, even if the voltage reference Vref were to fluctuate slightly over time, the digital signal would not be affected. There is no need for calibrated references in the circuit. This facilitates the use of the circuit when the rest of the system is idle, in which case no accurate references are available.

The precision of the measurement only depends on the stability of the reference voltage $V_{REF}$ during one measurement between times t1 and t2. The stability of $V_{REF}$ may be improved by adding a capacitor to the voltage source 357. However, $V_{REF}$, may be allowed to vary from measurements to measurements.

At the end of the measurement phase, at time t2, the reset signal 480 goes high, and the measure signal 490 goes low. The switches S1 and S2, are open, and the switches S3, S4 and S5 are closed. The integrator 351 is reset and the capacitors C1 and C2 are recharged by the bias current provided by the current generator 320. The voltage VA decreases below its steady-state value.

After time t2, the voltage VA starts increasing slowly to reach its steady state value at time t3, not shown in FIG. 3. At this point, the system is ready for the next measurement.

The system of FIG. 3 presents a number of advantages. The subtraction or removal of the $Q_{DC}$ component does not require the use of an amplifier. Instead, the DC removal is performed passively using the capacitor C2. This approach reduces power consumption and is easy to implement.

The capacitors C2 and C3 may be adjustable capacitors. By varying the capacitance of C2 it is possible to subtract the component $Q_{DC}$. By varying the capacitance of C3 it is possible to change the gain of the integrator to maximize the performance of the system.

The preferred types of LEDs used in this application have a forward voltage which might exceed the battery voltage when the battery is depleting. In the system 300, the charge provided to the LED during the measurement period does not arise from the current source 320 but mainly from the capacitor C1. As a result, the driving of the LED does not depend on the battery voltage Vbat. The node A can be driven above the battery voltage Vbat by providing an extra voltage headroom equal to Vref. This allows the LED to operate even if the battery is almost empty, (corresponding to a low battery voltage). In other words, the system will work even if the battery voltage is below the forward voltage of the LEDs. The circuit 300 acts as a charge-pump to provide the required forward voltage to the LED. As a result, no additional DC-DC converter (boost-converter or voltage-doubler) is required. This reduces the complexity of the circuit, and reduces its size.

The signal conditioning circuit (AFE) is based on a charge integrator instead of a TIA. In a TIA, the feedback loop of the operational amplifier is provided by a resistance, while in a charge integrator the feedback loop is provided by a capacitor. This is advantageous for low power systems generating small currents, as small capacitors can be used for the charge integrator. This is in contrast with TIAs which require a large resistance for low power applications. While resistors are relatively noisy elements, especially large ones, capacitors on the contrary do not generate noise by themselves.

FIG. 5 is another time chart showing the same signals as shown in FIG. 4. In FIG. 5, the visible time window extends over 20 ms and includes two measurement phases at time TA and TB, separated by a reset phase. In FIG. 5, it can be observed that between the two measurements, the output voltage 430 of the ADC has changed slightly.

FIG. 6 is yet another time chart showing the same signals as shown in FIGS. 4 and 5. In FIG. 6, the visible time window extends over 1 s and includes 100 measurements corresponding to 100 cycles. The output voltage 430 of the ADC is modulated with a modulation frequency of 2 Hz.

FIG. 7 shows a modified version of the system of FIG. 3. FIG. 7 shares many similar components to those illustrated in FIG. 3, so the same reference numerals have been used to represent corresponding components and their description will not be repeated for sake of brevity. In this example, the system 700 is provided with a calibration circuit 710 for cancelling the background current generated by the photodiode when the LED 310 is not active. Such a background current may have a dark-current component $I_{Dark}$ and an ambient light component, $I_{Ambient}$. The current $I_{Ambient}$ is associated with the charge $Q_{Ambient}$ generated by ambient light in the photodiode.

In the example of FIG. 7, the calibration circuit 710 is provided by a sample and hold circuit coupled to a current source. The current source may be provided by a transistor, such as an nMOS transistor 718 coupled to the node C. The sample and hold circuit includes an operational amplifier 712, a hold capacitor 714, and a switch 716. The operational amplifier 712 has a first input, for example an inverting input coupled to node E, and a second input for example a non-inverting input coupled to node D. The nMOS transistor 718 has a source coupled to the ground and a drain coupled to the node C. The gate of the nMOS transistor is coupled to the output of the operational amplifier 712 via the switch 716. The hold capacitor 714 has a first terminal coupled to the gate of the nMOS transistor and a second terminal connected to the ground.

In operation, the current source, provided by the transistor 718 may be calibrated just before the measurement in order to cancel the background current generated by the photodiode. The amplifier 712, the switch 716 and the transistor 718 form a calibration loop. During the reset phase, the switch 716 is closed, hence charging the hold capacitor 714. The switch 353 should be open while the switch 716 is closed. In this way, the circuit 710 has enough time to equate the current $I_{nMOS}$ into the nMOS transistor with $I_{Ambient}$ coming from the photodiode. The nMOS transistor acts as a controlled current source. When the loop is in regulation, $I_{nMOS}$ matches $I_{Ambient}$. During the measurement phase, the switch 716 is open. The hold capacitor 714 provides a gate-source voltage to the transistor 718, allowing the current $I_{nMOS}$ through the nMOS transistor 718 to be of a constant value and equal to the current $I_{Ambient}$, generated by the photodiode by ambient light. As a result, the current $I_{Ambient}$ is cancelled by the current $I_{nMOS}$.

A skilled person will appreciate that variations of the disclosed arrangements are possible without departing from the disclosure. Accordingly, the above description of the specific embodiment is made by way of example only and not for the purposes of limitation. It will be clear to the skilled person that minor modifications may be made without significant changes to the operation described.

What is claimed is:

1. An apparatus for monitoring a physiological parameter over a plurality of cycles, each cycle comprising a reset phase and a measurement phase, the apparatus comprising a circuit coupled to a light emitter and to a light receiver;
    wherein the circuit comprises a first capacitor having a first terminal coupled to the light emitter and a second terminal selectively coupled to a voltage reference and to a ground,
    the apparatus being adapted to couple the second terminal to the ground during the reset phase to charge the first capacitor so that a first voltage at the first terminal reaches an initial value and to couple the second terminal to the voltage reference during the measurement phase to increase the first voltage above the initial level, and then to discharge the first capacitor until the first voltage returns to the initial level so that the first capacitor provides a first charge to the light emitter during the measurement phase of each cycle, wherein the first charge remains substantially the same from cycle to cycle.

2. The apparatus as claimed in claim 1 wherein the circuit is adapted
    to integrate a second charge generated by the light receiver over a measurement period of the measurement phase;
    wherein the first charge provided over the measurement period of one cycle is substantially equal to another first charge provided to the light emitter over another measurement period of another cycle.

3. The apparatus as claimed in claim 2, wherein the circuit comprises an integrator coupled to the light receiver, the integrator being adapted to integrate an alternating current (AC) component of the second charge.

4. The apparatus as claimed in claim 2, wherein the circuit comprises a second capacitor coupled to the voltage reference via a second switch to subtract a direct current (DC) component of the second charge.

5. The apparatus as claimed in claim 4, wherein the second capacitor is adjustable.

6. The apparatus as claimed in claim 4, wherein the integrator is coupled to the light receiver; the light receiver comprising a first terminal and a second terminal; and wherein the light emitter is coupled to the first terminal via the first capacitor, and to the second terminal via the second capacitor.

7. The apparatus as claimed in claim 1, wherein
    the first capacitor is coupled to the voltage reference via a first switch to drive the light emitter.

8. The apparatus as claimed in claim 1, wherein the first charge is proportional to a voltage provided by the voltage reference.

9. The apparatus as claimed in claim 3, wherein the integrator comprises an operational amplifier coupled to a capacitor.

10. The apparatus as claimed in claim 1, comprising a calibration circuit for cancelling a background current generated by the light receiver.

11. The apparatus as claimed in claim 10, wherein the calibration circuit comprises a sample and hold circuit coupled to another current source.

12. A wearable device comprising an apparatus for monitoring a physiological parameter over a plurality of cycles, each cycle comprising a reset phase and a measurement phase, the apparatus comprising a circuit coupled to a light emitter and to a light receiver;
wherein the circuit comprises a first capacitor having a first terminal coupled to the light emitter and a second terminal selectively coupled to a voltage reference and to a ground, the apparatus being adapted to couple the second terminal to the ground during the reset phase to charge the first capacitor so that a first voltage at the first terminal reaches an initial value and to couple the second terminal to the voltage reference during the measurement phase to increase the first voltage above the initial level, and then to discharge the first capacitor until the first voltage returns to the initial level so that the first capacitor provides a first charge to the light emitter during the measurement phase of each cycle, wherein the first charge remains substantially the same from cycle to cycle.

13. A circuit for use with a light emitter and a light receiver, wherein the circuit is adapted to operate over a plurality of cycles, each cycle comprising a reset phase and a measurement phase,
wherein the circuit comprises a first capacitor having a first terminal coupled to the light emitter and a second terminal selectively coupled to a voltage reference and to a ground, the circuit being adapted to couple the second terminal to the ground during the reset phase to charge the first capacitor so that a first voltage at the first terminal reaches an initial value and to couple the second terminal to the voltage reference during the measurement phase to increase the first voltage above the initial level, and then to discharge the first capacitor until the first voltage returns to the initial level so that the first capacitor provides a first charge to the light emitter during the measurement phase of each cycle, wherein the first charge remains substantially the same from cycle to cycle.

14. The circuit as claimed in claim 13, wherein the first capacitor is coupled to the voltage reference via a first switch to drive the light emitter.

15. The circuit as claimed in claim 13, comprising an integrator coupled to the light receiver, the integrator being adapted to integrate an alternating current (AC) component of a second charge.

16. The circuit as claimed in claim 13, comprising a second capacitor coupled to the voltage reference via a second switch.

17. A method for monitoring a physiological parameter over a plurality of cycles, each cycle comprising a reset phase and a measurement phase, the method comprising
providing a light emitter and a light receiver;
providing a circuit comprises a first capacitor having a first terminal coupled to the light emitter and a second terminal selectively coupled to a voltage reference and to a ground,
coupling the second terminal to the ground during the reset phase to charge the first capacitor so that a first voltage at the first terminal reaches an initial value
coupling the second terminal to the voltage reference during the measurement phase to increase the first voltage above the initial level, and then to discharging the first capacitor until the first voltage returns to the initial level so that the first capacitor provides a first charge to the light emitter during the measurement phase of each cycle, wherein the first charge remains substantially the same from cycle to cycle.

18. The method as claimed in claim 17, comprising
integrating a second charge generated by the light receiver over a measurement period of the measurement phase;
wherein the first charge provided over the measurement period of one cycle is substantially equal to another first charge provided to the light emitter over another measurement period of another cycle.

19. The method as claimed in claim 18, wherein the second charge comprises an alternating current (AC) component and a direct current (DC) component; the method comprising integrating the AC component to obtain an integrated signal.

20. The method as claimed in claim 19, comprising deriving the physiological parameter based on the integrated signal.

21. The method as claimed in claim 19, comprising subtracting the DC component, wherein subtracting the DC component is performed passively.

22. The method as claimed in claim 21, wherein subtracting the DC component comprises charging a second capacitor coupled to the light emitter.

23. The method as claimed in claim 17, comprising charging the first capacitor coupled to the light emitter to increase a voltage across the light emitter.

24. The method as claimed in claim 17, comprising cancelling a background current generated by the light receiver.

25. The method as claimed in claim 17, wherein the first charge is proportional to a reference voltage provided by the voltage reference.

* * * * *